(12) United States Patent
Taylor et al.

(10) Patent No.: US 8,945,181 B2
(45) Date of Patent: Feb. 3, 2015

(54) SUTURE RETENTION DEVICES AND ASSOCIATED PRODUCTS AND METHODS

(71) Applicant: Cook Medical Technologies LLC, Bloomington, IN (US)

(72) Inventors: James Taylor, Bloomington, IN (US); Benjamin Fisher, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 13 days.

(21) Appl. No.: 13/791,998

(22) Filed: Mar. 9, 2013

(65) Prior Publication Data

US 2013/0238024 A1 Sep. 12, 2013

Related U.S. Application Data

(60) Provisional application No. 61/609,287, filed on Mar. 10, 2012.

(51) Int. Cl.
*A61B 17/04* (2006.01)
*A61B 17/10* (2006.01)
(Continued)

(52) U.S. Cl.
CPC ......... *A61B 17/0401* (2013.01); *A61B 17/0487* (2013.01); *A61B 17/0218* (2013.01); *A61B 2017/0417* (2013.01); *A61B 2017/0448* (2013.01); *A61B 2017/0464* (2013.01); *A61B 2017/06052* (2013.01); *A61B 2017/0409* (2013.01)
USPC ......... 606/232; 606/138; 606/139; 24/115 N; 24/129 A

(58) Field of Classification Search
CPC ........... A61B 17/0401; A61B 17/0469; A61B 17/06482; A61B 17/0483; A61B 2017/0409; A61B 2017/0414; A61B 2017/0451; A61B 2017/0459; A61B 2017/0462

USPC ......... 606/232, 139, 148; 132/323; 24/115 N, 24/129 A; 289/13, 17; 43/44.9, 44.91, 43/44.94, 44.95

See application file for complete search history.

(56) References Cited

U.S. PATENT DOCUMENTS

| | | | |
|---|---|---|---|
| 5,537,776 A * | 7/1996 | Gilard, Sr. | 43/42.49 |
| 2003/0191497 A1 | 10/2003 | Cope | |
| 2003/0195562 A1 * | 10/2003 | Collier et al. | 606/232 |
| 2006/0004409 A1 | 1/2006 | Nobis et al. | |

(Continued)

FOREIGN PATENT DOCUMENTS

| | | |
|---|---|---|
| WO | WO 2005/112786 A3 | 12/2005 |
| WO | WO 2006/111394 A2 | 10/2006 |
| WO | WO 2007/124772 A1 | 11/2007 |

*Primary Examiner* — Todd Manahan
*Assistant Examiner* — Charles A Lutzow, III
(74) *Attorney, Agent, or Firm* — Woodard, Emhardt, Moriarty, McNett & Henry LLP

(57) ABSTRACT

A suture retention device includes a stack of suture engaging members which can be provided by coils or other segments of a spring. A suture engages with the stack so as to permit travel of the retention device along the suture in one direction more facilely than travel along the suture in the other direction. The retention device can include a housing that encloses the spring or other stack structure, and the suture can pass from a first hole in the housing, through the suture engaging members, and to a second hole in the housing. A suture anchor can be attached to the suture, and the resulting assembly can be combined with a needle designed to introduce the anchor and suture into patient tissue, e.g. in the conduct of a gastropexy procedure.

27 Claims, 11 Drawing Sheets

(51) Int. Cl.
*F16G 11/00* (2006.01)
*F16L 3/00* (2006.01)
*H02G 7/05* (2006.01)
*A44B 1/04* (2006.01)
*A44B 11/25* (2006.01)
*A61B 17/02* (2006.01)
*A61B 17/06* (2006.01)

(56) References Cited

U.S. PATENT DOCUMENTS

| | | | |
|---|---|---|---|
| 2006/0004410 A1* | 1/2006 | Nobis et al. | 606/232 |
| 2007/0083235 A1* | 4/2007 | Jervis et al. | 606/232 |
| 2008/0306511 A1* | 12/2008 | Cooper et al. | 606/232 |
| 2009/0018552 A1* | 1/2009 | Lam et al. | 606/139 |
| 2009/0318938 A1* | 12/2009 | Hathaway et al. | 606/144 |

* cited by examiner

SUTURE RETENTION DEVICES AND ASSOCIATED PRODUCTS AND METHODS

REFERENCE TO RELATED APPLICATION

This application claims the benefit of U.S. Provisional Application No. 61/609,287, filed Mar. 10, 2012, entitled "SUTURE RETENTION DEVICES AND ASSOCIATED PRODUCTS AND METHODS", which is hereby incorporated by reference.

FIELD OF THE INVENTION

The present invention relates generally to medical devices, and in certain particular aspects to devices through which a suture is passed and which can selectively translate along or resist translation along the suture.

BACKGROUND

In the field of medicine there are often occasions in which a suture needs to be secured in a position or a condition selected by a doctor or other attending health care provider. Examples occur in surgeries in which a suture is used to approximate two different segments of tissue to one another, for example during a gastropexy procedure. In traditional gastropexy, the stomach wall of a patient is secured against the inner surface of the abdominal wall by one or more sutures passing from external of the patient, through the abdominal wall, through the stomach wall, and into the stomach. Oftentimes, an anchor, such as a T-bar anchor, is connected to that portion of the suture that resides in the stomach. With the anchor positioned against the inner stomach wall, the suture is tensioned from outside the patient to pull the stomach wall against the abdominal wall. At that point, the suture needs to be secured at a position external of the patient to maintain the applied tension. For these purposes, it is known to either stitch the suture to the skin of the patient, or to use a suture retention device connected to the suture that abuts against the skin of the patient and holds the tension. After securing an extended segment of the stomach against the abdominal wall with several such suture-anchor arrangements, a number of useful procedures can be conducted, usually involving intubating the stomach of the patient by passing a tube through the region where the abdominal wall and stomach that are held against one another.

It is desirable to conduct gastropexy surgeries and other similar tethering or tissue anchoring surgeries rapidly, efficiently, and safely. To accomplish these ends, there are needs for improved and alternative suture retention devices, and associated assemblies and methods.

SUMMARY

In certain aspects, the present invention provides devices and methods for retaining surgical tethers such as sutures. The devices and methods can involve a tether engaging stack structure including at least first and second adjacent stack members, such as coils of a spring, positionable external of a patient and operably coupled to a surgical tether that can be passed into a patient. The operable coupling can include a frictional securement of the position of the surgical tether by a clamping force between adjacent stack members of the stack structure. It should be appreciated that while not limited to such, embodiments of the present invention can be useful for performing a gastropexy procedure or other procedure in which an organ wall or other tissue wall is to be engaged by a tissue anchor and retained in a displaced condition (e.g. against another organ wall or tissue wall).

In one embodiment, provided is a surgical tether retention device that includes a housing having a first end and a second end, the first end defining a first end wall surface configured for receipt against an external patient surface and a first end wall opening. A tether engaging stack structure is retained by the housing, the stack structure including at least first and second adjacent stack members. A surgical tether is provided and has a housed tether portion extending through the housing in a path from the first end wall opening to a second opening spaced from the first end wall opening. The surgical tether has a first external tether portion extending out of the first end wall opening in a first direction external of the housing. The surgical tether has a second external tether portion extending out of the second opening in a second direction different from the first direction and external of the housing. The housed tether portion includes at least one tether segment received between the first stack member and the second stack member. The housed tether portion is cooperatively associated with the tether engaging stack so as to urge the first and second stack members away from one another when the housing is urged along the surgical tether in the first direction and to urge the first and second stack members toward one another when the housing is urged along the surgical tether in the second direction. The stack structure can include an integral structure, such as a spring, providing the first and second stack members.

In another embodiment, provided is a medical device that includes an elongate surgical tether and a tether engaging structure. The tether engaging structure includes at least first and second adjacent members and is cooperatively associated with the elongate surgical tether so as to compressively engage and retain the position of the tether relative to the stack when the tether is forced in a first direction relative to the stack but to allow travel of the suture through the stack when the tether is forced in a second direction relative to the stack. The tether engaging structure can include a spring providing the at least first and second adjacent members, and preferably one or more additional members. The device can also include a first wall member having a first wall member opening, and the surgical tether can be positioned passing through the first wall member opening. A tether anchoring element, such as a T-tag, can be attached to the surgical tether. The medical device can also include a needle configured to advance the surgical tether through patient tissue and, where the device includes a tether anchoring element, the anchoring element can be at least partially received within a lumen of the needle. In several embodiments, the stack structure can include at least a third stack member, wherein the surgical tether is received between the first and second stack members, and wherein the surgical tether is looped around at least the third stack member. Additionally, the surgical tether can have portions extending away from at least the third stack member, around which the surgical tether is looped, from opposing sides of at least the third stack member.

Another embodiment provides a device for securing a surgical tether that includes a surgical tether, a tether anchoring element attached to the surgical tether, and a tether retention device received on the surgical tether. The tether retention device includes a spring having a plurality of spring segments adjacent to one another, the plurality of spring segments including at least first and second spring segments adjacent to one another and at least a third spring segment. The tether retention device further includes a housing retaining the spring, the housing having a first wall portion defining a first opening and a second wall portion defining a second opening.

The surgical tether passes through the housing of the tether retention device from the first opening to the second opening thereby providing a housed tether segment within the housing. The housed tether segment is received between the first and second spring segments and looped at least one time around the third spring segment. In certain embodiments, tension can be applied to the tether in a first direction so as to tension and expand the spring to reduce or eliminate a clamping force applied to the suture by a coil or coils of the spring, and allow the suture to travel through the spring. Release of the tension applied to the tether in the first direction allows the spring to contract to or toward its relaxed condition, such that the suture is again clamped between the first coil and one or more adjacent coils of the coil spring. Additionally, in certain embodiments, tension can be applied to the tether in a second direction that differs from the first direction, so as to apply compressive force to the spring and cause or increase a clamping force of the spring on the tether, to cause resistance to travel of the tether through the spring. The housing preferably encloses or surrounds the spring, e.g. so as to prevent direct contact of the spring by a user or by patient tissue in use. In several instances, the device can also comprise at least a fourth spring segment located between the second and third spring segments, and wherein the housed tether segment extends over an external surface of the fourth spring segment without looping around the fourth spring segment. Additionally, the device may comprise at least a fifth spring segment located adjacent the third spring segment, and wherein a portion of the surgical tether passes over an internal surface of the fifth spring segment without looping around the fifth spring segment.

Any suture or sutures disclosed herein may be any suitable bioabsorbable or non-bioabsorbable, multi-filament or monofilament suture. Similarly, any disclosed suture anchor(s) may, for example, be a "T-bar" or "T-tag" device or other device including an elongate rod structure, as is known for anchoring the end portion of a suture against a tissue wall, for example when tensioning the suture to approximate first and second tissues to one another, e.g. in a gastropexy procedure. Suitable suture anchors are known including for example those described in U.S. Pat. Nos. 5,123,914, 6,110,183 and 6,699,263, and those commercially available from Cook Medical, Bloomington, Ind. in products sold under the trade name Cope Gastrointestinal Suture Anchor Set.

It is also contemplated, and will be appreciated by those of skill in the art, that the herein disclosed surgical tether retention devices, not limited to those partially and/or entirely illustrated in the provided figures, may be used with the needle assembly and suture anchoring system illustrated and explained with regards to FIG. 6. Similarly, any of the disclosed tether retention devices may have a release mechanism, such as the manual release mechanism illustrated in FIG. 7.

The association of a surgical tether with tether engaging stack structure is arranged so that the application of a pull force on the surgical tether and/or pushing on the tether engaging stack structure in a direction retrograde (away from an anchor or the patient) along the surgical tether, or both, puts portions of tether engaging stack structure in compression. On the other hand, the application of a pulling force on surgical tether in a direction antegrade (toward an anchor or the patient) along surgical tether, or both, can longitudinally extend or expand portions of the tether engaging stack structure by putting the same in tension, thereby permitting travel of the surgical tether relative to the tether engaging stack structure. In several embodiments, modes of associating surgical tether with a tether engaging stack structure provide an arrangement wherein antegrade movement of the tether engaging stack structure is permitted due to tensile force imparted to expand portions of the tether engaging stack structure but retrograde movement of the tether engaging stack structure is prevented due to an inherent compressive force and/or bias between portions of the tether engaging stack structure, Portions of surgical tethers described herein may, in several instances, comprise looped segments that can loop around a portion of a tether engaging stack structure, such as a spring coil. In these instances, the loop(s) may comprise a left-handed helix or a right-handed helix and may extend along a portion of the tether engaging stack structure in a direction towards or away from a secured end of the tether engaging stack structure or perpendicular to a longitudinal axis of the tether engaging stack structure. As will be appreciated, the direction in which the surgical tether is looped and/or extends along a portion of the tether engaging stack member may be arranged so that upon application of a pulling motion to slide portions of tether engaging stack member along a length of the surgical tether, portions of the surgical tether migrate from a first position to a second position along a length of one or more of the stack members of the tether engaging stack structure. In some instances, portions of surgical tether can migrate towards or away from a secured end of the tether engaging stack structure. As disclosed herein, associations of surgical tether(s) and tether engaging stack structure(s) may be arranged such that a risk of the surgical tether becoming disassociated with tether engaging stack structure during use of the device is decreased and/or eliminated. For example, the distance a looped portion must migrate along a stack member before becoming disassociated with the stack member may be increased and/or the ends of the of the stack members may be closed, such as by the stacking members comprising closed loops and/or the ends of a helically wound tether engaging stack structure being coupled to adjacent one or more adjacent stack members so that a looped portion of a surgical tether is not free to slide off the end of the helical structure. Alternatively or additionally, the surgical tether may be looped in a specific helical fashion and/or along a particular direction of a stack member.

As well, in embodiments employing a spring for a tether engaging structure, the spring may be a helically wound spring as illustrated herein, a flat spring, or any other spring configuration providing a plurality of segments for achieving the structural and functional requirements described herein. Any spring identified herein may, for example, be comprised of or constituted from a synthetic polymeric material or a suitable metal such as stainless steel, or combinations thereof, and may be positioned in any suitable orientation in the housing or relative to a patient surface. Likewise, other components of the suture retention device, of the needle or its components, can be comprised of or constituted from any suitable material including metal, polymeric material, or combinations thereof. The use of these and other variations will be within the purview of those of ordinary skill in the art.

Any reference to a housing or housing herein includes those arranged to enclose or surround one or more tether engaging stack structures, such as springs, to prevent user or patient contact therewith. The housing(s) could be omitted or other housing or wall arrangements could be used which partially shield the tether engaging stack structure(s) or partially enclose a portion or portions of the tether engaging stack structure(s). Disclosed housing(s) can also provide at least one surface disposed to face the patient in use, and at least one surface opposite thereto It is also contemplated that housing portions disclosed herein may be arranged for coupling to one another and/or a tether engaging stack structure, such as by use of mechanical attachments including but not limited to bonding, screws, and/or interference/friction fitting portions. For example, one or more housing portions may comprise an elongate portion arranged to cooperate with a recess of the opposing housing when the housing portions are brought into cooperation. In several embodiments, the elongate portion may be secured within the recess with a mechanical fastener, as mentioned, such as an adhesive.

Components of disclosed embodiments, such as surgical tethers (e.g., sutures), anchors, tether engaging stack structures (e.g., springs), housings, and needle assemblies may be combined in various combinations or singly and enclosed within a sterile medical package(s). For example, at least two or more or all of these components can be arranged to operate with each other and may be combined and sealed within a package to be sold as a single medical product. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additional embodiments include methods of use of devices as disclosed herein to secure a position of a surgical tether, and methods of manufacture of devices as disclosed herein. Still further embodiments of the invention as well as features and advantages associated therewith will be apparent to those skilled in the pertinent art from the descriptions herein.

DETAILED DESCRIPTION

Figure 1:
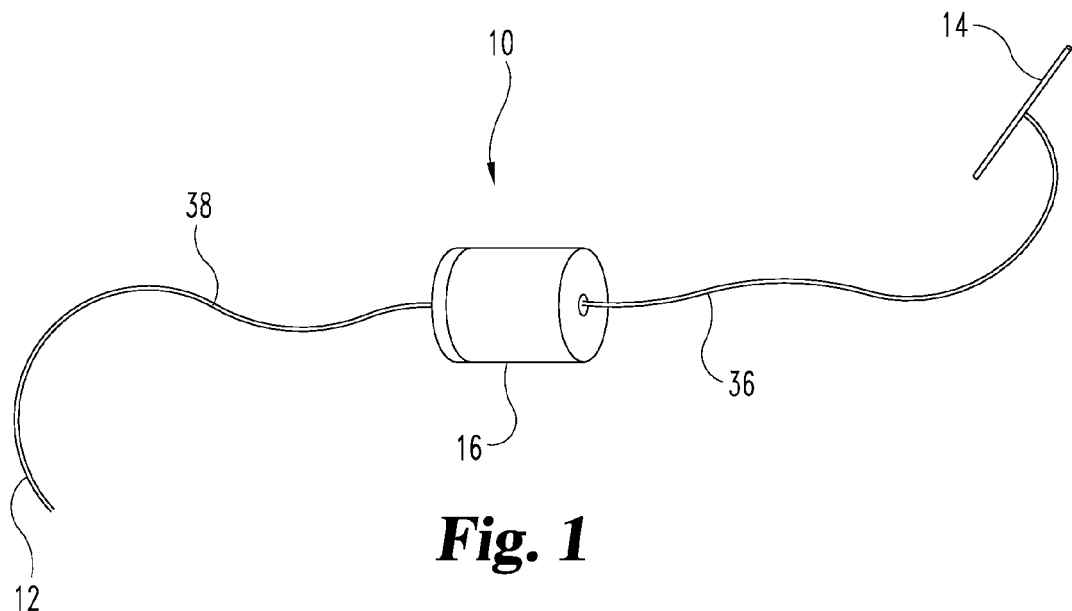
FIG. 1 provides a perspective view of one embodiment of a suture retention device in association with a suture and suture anchor.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. At least one embodiment of the invention is shown in great detail, although it will be apparent to those skilled in the relevant art that some features that are not relevant to the present invention may not be shown for the sake of clarity.

With reference to FIG. 1, shown is one embodiment of a suture retention device of the present invention and elements that may be associated therewith. In particular, shown is suture retention device 16 having associated therewith a suture 12 and a suture anchor 14. Suture 12 may be any suitable bioabsorbable or non-bioabsorbable, multi-filament or monofilament suture, and suture anchor 14 may, for example, be a "T-bar" or "T-tag" device or other device including an elongate rod structure, as is known for anchoring the end portion of a suture against a tissue wall, for example when tensioning the suture to approximate first and second tissues to one another, e.g. in a gastropexy procedure. Suitable suture anchors are known including for example those described in U.S. Pat. Nos. 5,123,914, 6,110,183 and 6,699,263, and those commercially available from Cook Medical, Bloomington, Ind. in products sold under the trade name Cope Gastrointestinal Suture Anchor Set.

Figure 2:
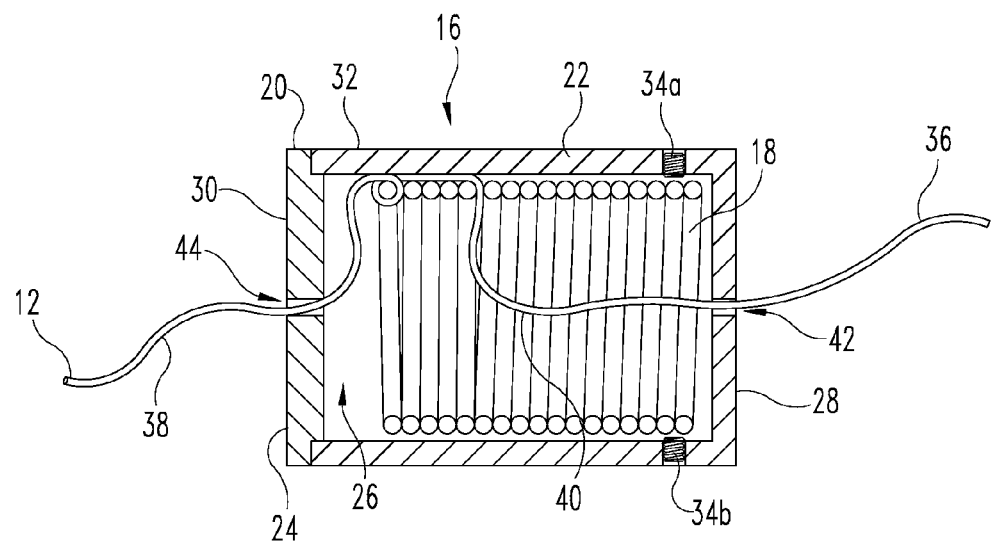
FIG. 2 provides a cross-sectional view of the suture retention device of FIG. 1 taken along a central longitudinal plane.

With reference now to FIG. 2 in conjunction with FIG. 1, shown in FIG. 2 is a cross-sectional view taken longitudinally along the central axis of suture anchor device 16. Anchor device 16 includes a coil spring 18 providing a suture retention stack including a plurality of closely spaced or adjacent stack members, retained with a housing 20. Housing 20 includes a first generally cylindrical housing member 22 and a second housing member 24 capping housing member 22. While the illustrated housing 20 encloses or surrounds spring 18 to prevent user or patient contact therewith, the housing could be omitted or other housing or wall arrangements could be used which partially shield the spring 18 or partially enclose a portion or portions of the spring 18. The illustrated housing 20 defines an internal chamber 26 in which spring 18 is received. Spring 18 can be received in internal chamber 26 in a slip-fit or other close-fitting relationship that allows movement, preferably along a longitude of the spring, of at least some spring segments associated with suture 12 for suture release and compression functions as described herein. A close-fitting relationship of the spring 18 with the sidewalls of chamber 26 is desired so as to prevent any exaggerated laterally-directed bending of spring 18 during use of device 16. Internal chamber 26 provides an amount of longitudinal head space beyond an end of the spring 18 in a direction in which the spring 18 is to be expandable as described herein (occurring to the left end of chamber 26 in FIG. 2), to leave room for such expansion. Housing 20 provides a first end surface 28 disposed to face the patient in use, and a second end surface 30 opposite thereto. Housing 20 includes sidewalls 32 extending between end portion 28 and end portion 30. Device 16 also includes set screws 34a and 34b penetrating sidewalls 32 and contacting spring 18 under compression along a portion thereof to fix the location of spring 18 within chamber 26. It will be understood that other modes of fixing the relative location of spring 18 could also be used, including for example bonding or other mechanical attachments.

Suture 12 as associated with device 16 includes a first suture portion 36 located on a first (patient-facing) side of device 16, a second suture portion 38 located on the opposite side of device 16 relative to portion 36, and a third segment 40 occurring within housing 20. As associated with housing 20, suture 12 passes through opening 42 in the end wall defining surface 28, through chamber 26, and through opening 44 in the end wall defining surface 30. As shown, the internalized suture segment 40 is associated with spring 18 through interaction with coils thereof, one embodiment of which is more particularly described below in association with the figures.

Figure 3:
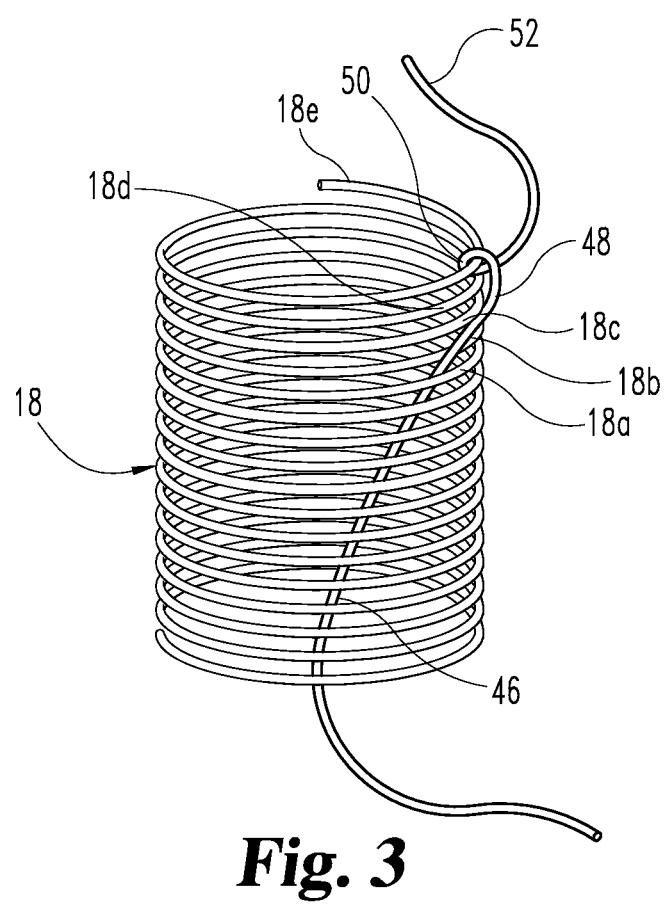
FIG. 3 provides a partial cut-away perspective view of portions of the device depicted in FIGS. 1 and 2 with a spring in an extended condition.
Figure 4:
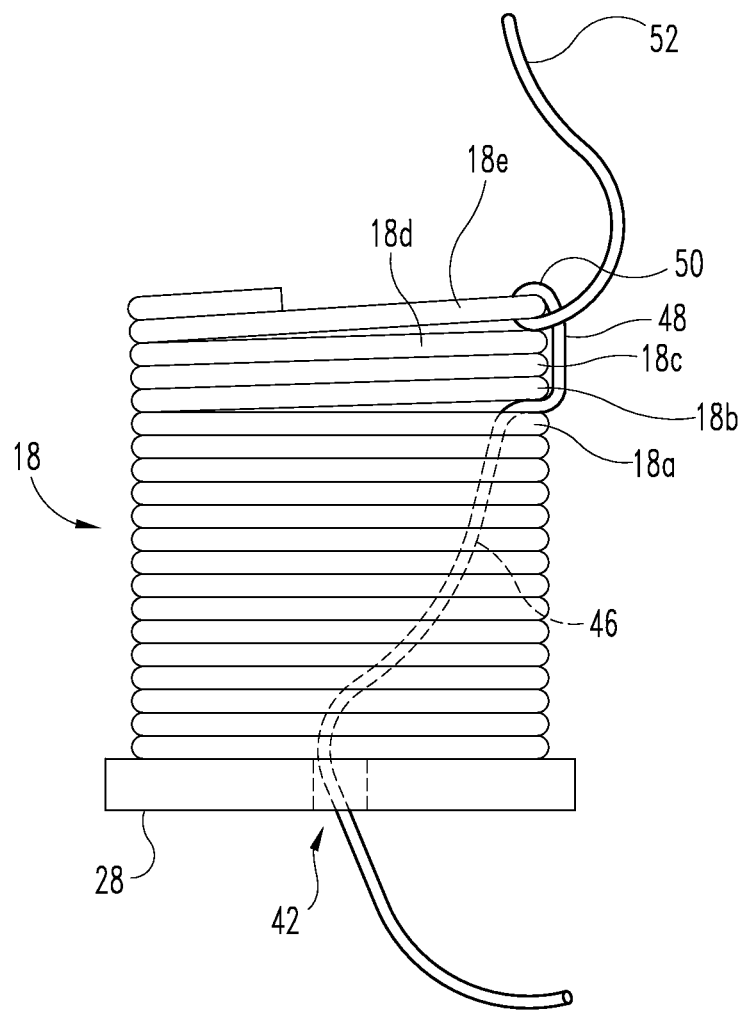
FIG. 4 provides a partial cut-away side-elevational view of portions of the device of FIGS. 1 and 2 with a spring in a relaxed, contracted condition.

In that regard, referring now to FIGS. 3 and 4, FIG. 3 shows the spring 18 in a somewhat extended or expanded configuration to better illustrate the pattern of association of suture 12, and in particular its segment 40, with spring 18, while FIG. 4 shows the spring 18 in its relaxed configuration having individual coils thereof abutting one another and compressing the suture 12 at positions between spring coils. In the illustrated embodiment, the suture segment 40 includes a first segment portion 46 extending through a lumen defined by coil spring 18. Segment 40 then passes between adjacent spring coils 18a and 18b to thereby extend to a second segment portion 48 that travels external of the spring 18 lumen and along the external surface of spring coils 18b, 18c, and 18d. Segment 40 has a third segment portion 50 that is looped around spring coil 18e at least one time, although use of either single loop or multiple loops, e.g. 2, 3, or 4 loops. This looping of segment 40 around a coil or coils of spring 18 occurs in certain embodiments in a region proximate to the proximal end of spring 18, and can include a looping around the final end coil segment of the spring alone or in combination with one or more other adjacent coils. Thereafter, the internalized suture segment 40 extends as a fourth segment portion 52 from the loop(s) segment portion 50 and ultimately through opening 44. In the preferred embodiment, the spring 18 in its relaxed state has closely abutting coils so as to provide compression on suture segment 40 at locations where segment 40 passes between adjacent ones of its coils.

The association of suture 12, and in particular its internalized segment 40, with spring 18 is arranged so that the application of a pull force on suture portion 36, for example by pulling on suture portion 36, pushing device 16 in a direction retrograde (away from anchor 14 or the patient) along suture 12, or both, puts spring 18 in compression. When this occurs, additional compression is imparted to suture segment 40 at the location or locations at which it passes through adjacent coils of spring 18, thus resisting travel of the suture 12 relative to spring 18 and thus relative to device 16. In certain embodiments, the suture retention device 16 can thereby resist any significant travel (e.g. travel of more than about 0.5 cm, or travel of more than about 0.1 cm) of the suture relative to the spring and/or housing even upon the application of 20 Newtons of force by tensioning suture 12 so as to compress spring 18.

On the other hand, the application of a pulling force on segment 38 of suture 12, for example by pulling on suture portion 38, pushing device 16 in a direction antegrade (toward anchor 14 or the patient) along suture 12, or both, longitudinally extends or expands the coil spring 18 by putting the same in tension, thereby permitting travel of the suture 12 relative to the spring 18 and device 16. In one operative mode, the expansion of the spring 18 upon the application of this tension separates at least some of the coils of spring 18. In this regard, while travel of the suture 12 is permitted during application of this pull force, the sliding frictional engagement of coil spring 18e by loop(s) is sufficient to transmit enough of the pull force to coil spring 18 to achieve separation of the necessary coils to ease suture travel. Continued pulling force applied to suture 12 at segment 38 continues translation of suture 12 through device 16, thus allowing an operation in which device 16 is translated antegrade along suture 12 toward suture anchor 14. This can be used in a securing procedure for anchor 14 as discussed further below. In certain embodiments, the suture retention device 16 allows travel of the suture 12 relative to the housing 20 and/or spring 18 upon the application of no greater than about 10 Newtons of force by tensioning suture 12 so as to expand spring 18, e.g. by a pull force applied to segment 38. When the pull force applied to segment 38 is discontinued, spring 18 returns to its relaxed configuration (see FIG. 4). Any subsequent attempt to force the device 16 retrograde along suture 12 will again put spring 18 in compression and cause a resistance to retrograde travel along suture 12 as discussed above.

It will be understood that FIGS. 1 to 4 depict one mode of associating suture 12 with spring 18 to provide an arrangement wherein antegrade movement of device 16 is permitted due to tensile force imparted to expand the spring 18 but retrograde movement of the device 16 is prevented due to compressive force applied to spring 18. In certain embodiments, as exemplified in the illustrated embodiment, the suture 12 will be looped around a coil or a group of coils (typically adjacent coils) to provide a sliding frictional engagement of the coil(s) during application of a force to translate the device 16 antegrade along suture 12, and to provide a retaining frictional engagement (with essentially no sliding of the suture 12) of the coil(s) during application of a force that would tend to translate the device 16 retrograde along suture 12. This retaining frictional engagement can apply a compressive force to spring 18 and thereby apply compression or further compression upon segments of suture that pass between coils that occur antegrade on the spring 18 relative to the point of frictional engagement by the loop(s) (e.g. on the suture segment that extends between coils 18a and 18b of FIGS. 3 and 14). Variations of these and other suture travel patterns through and/or around coils of spring 18, or other springs, will be within the purview of those of ordinary skill in the field given the teachings herein.

Figure 5:
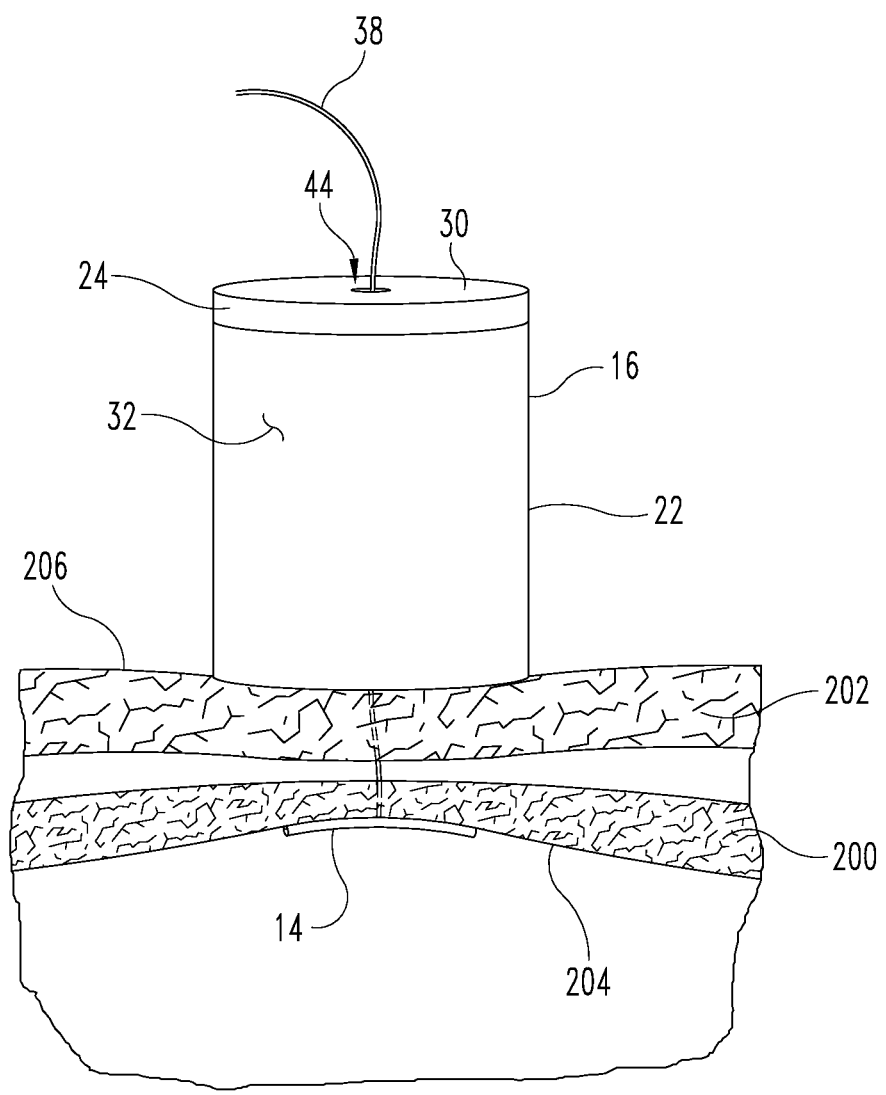
FIG. 5 provides an illustration of an implanted suture anchoring system incorporating the suture retention device of FIGS. 1 to 4.

FIG. 5 provides an illustration of an implanted suture anchoring system incorporating the suture retention device of FIGS. 1 to 4, as can occur in a gastropexy procedure in which a stomach wall 200 is held close to or against an abdominal wall 202. Particularly, this is accomplished by suture 12 passing through both walls 200 and 202, with anchor 14 positioned against an inner wall surface 204 of stomach wall 200, and suture retention device 16 received against the external surface 206 (e.g. skin) of the patient and secured to suture 12. The suture 12 is held in tension, with the suture retention device 16 secured thereon and preventing retrograde travel of device 16 along suture 12 through the interaction of the suture 12 with spring 18 (see FIGS. 2-4) of device 16. Antegrade travel of device 16 along suture 12 is permitted as discussed above, which has allowed the physician or other health care provider to move device 16 along suture 12 down toward and against the external surface 206.

Figure 6:
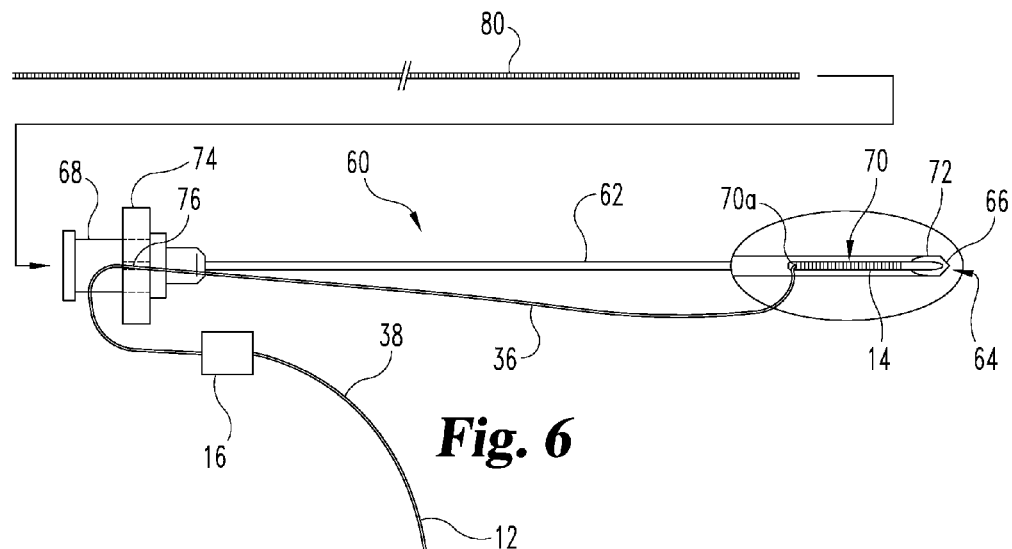
FIG. 6 provides a partially-enlarged perspective view of a needle assembly including a suture anchoring system incorporating the suture retention device of FIGS. 1 to 5.

With reference now to FIG. 6, shown is a needle assembly 60 incorporating a suture retention combination, such as that as shown in FIG. 1. Needle assembly 60 includes a needle cannula 62 defining a lumen 64 therethrough and having a tissue penetrating distal tip 66 and a proximal hub 68. Hub 68 can optionally incorporate a mechanism for connection to a syringe or other fluid delivery device, for example an internal thread pattern as associated with conventional Luer-lock connectors. Needle cannula 62 has a distal region having a slot 70 defined therein communicating with lumen 64 and extending distally to the distal edge 72 of cannula 62. Suture anchor 14 is received within lumen 64 with a portion of anchor 14 exposed through slot 70. Suture 12 is received against an upper edge 70a of slot 70, where upper edge 70a is so configured as to avoid cutting or tearing suture 12 during use of assembly 60. Suture 12 passes adjacent to and external of needle cannula 62 to the region of hub 70. Desirably, suture 12 is removably secured in the region of the hub to ease use of needle assembly 60 during advancement of needle cannula 62 into patient tissue. This securement can be accomplished in any suitable fashion, for example with removable tape, bonding agents, or reversible mechanical fasteners. In the illustrated embodiment, a mechanical fastener is provided by an annular member 74 mounted around hub 70 and having a slit 76 communicating with an outer periphery thereof, for receiving and frictionally securing the position of suture 12 in the slit 76. Suture 12 can be pulled to disengage suture 12 from slit 76 when desired. For these purposes annular member 74 can be made of a polymeric material, desirably an elastomeric material, such as silicone rubber. Device 16 is received on suture 12, e.g. as discussed hereinabove. Needle assembly 60 can also be provided (e.g. in a kit) in conjunction with an elongated pusher 80 such as a straight wire guide structure, which can be passed through hub 70 and distally down the lumen 64 to deploy anchor 14 after the needle cannula 62 has been advanced to the desired position.

In use, needle assembly 60 can be used to advance and deploy anchor 14 in a desired location in a patient. In a gastropexy procedure, the stomach of the patient is typically insufflated, and the distal tip of the needle cannula 62 is passed through the patient skin and abdominal wall and into the stomach. The suture anchor 14 is then deployed, for example using pusher 80 passed through the lumen 64 of cannula 62. The needle can then be withdrawn, leaving anchor 14 implanted within the stomach of the patient and suture 12 threading through the needle tract and out of the patient. Suture retention device 16 is attached to the suture external of the patient and spaced from the patient's skin. Retention device 16 can then be slid down suture 12 toward the skin of the patient, and lodged against the skin of the patient to leave suture 12 in tension, with stomach wall 200 pulled toward and against abdominal wall 202. Most often, several (e.g. 2, 3, or 4) such anchors are set in place in the stomach of the patient, to approximate a region of the stomach wall against the abdominal wall. Surgical procedures accessing the stomach can then be conducted through the approximated stomach wall region, for instance to implant feeding tubes or tubes for other therapeutic or diagnostic medical purposes.

Figure 7:
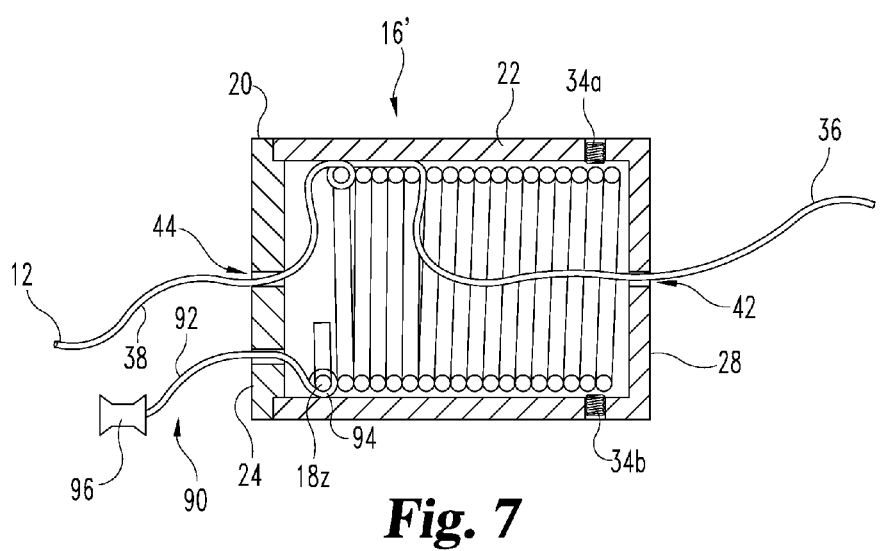
FIG. 7 provides a cross-sectional view, taken upon a central longitudinal plane, of a suture retention device having features additional to those of the suture retention device of FIGS. 1 to 5 to allow for selective retrograde travel of the device along a suture.

Referring now to FIG. 7, shown in another embodiment of a suture retention device 16' of the invention. Suture retention device 16' includes features similar to those of device 16 of FIGS. 1-5, which are similarly numbered. Suture retention device 16' also includes a manual release mechanism which, when actuated, allows a user to slide device 16' along suture 12 in the direction that would otherwise be resisted as discussed hereinabove. Manual release mechanism 90 includes a pull tether 92, for example a segment of suture material, that is attached to spring coil 18z, for example including a looped tether segment 94 around coil 18z (e.g. formed in tying tether 92 to coil 18z). Release mechanism 90 also desirably includes a knob 96 or other grip element attached to pull tether 92. Pulling on knob 96 tensions spring 18, thereby urging a separation of coils 18z and 18a-18e that can counteract the tendency for travel of device 16' along suture 12 in the direction of suture segment 38 to compress spring 18 and clamp the suture 12, thus allowing travel of device 16' in such direction during actuation of release mechanism 90. In this manner, if a physician or other user, in setting the final position of device 16', wishes to move device 16' away from anchor 14 (e.g. away from the patient), knob 96 can be pulled during such movement to allow repositioning of device 16'. Release of knob 96 will put device 16' again into its condition in which travel in the direction away from anchor 14 is prevented. If desired, after device 16' has been placed in its final, desired position, tether 92 can be cut to remove knob 96 to help avoid any accidental movement of device 16' away from anchor 14 or release of suture 12 during subsequent procedural steps or convalescence periods.

Figure 8:
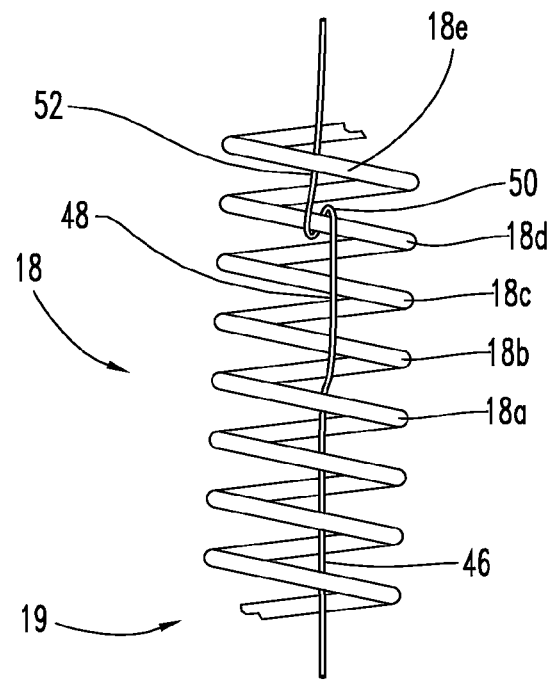
FIG. 8 provides a partial cut-away side-elevational view of another arrangement of a spring in an extended condition.
Figure 9:
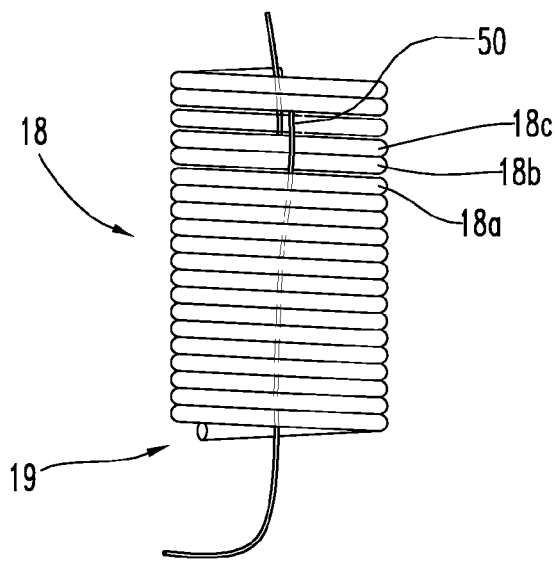
FIG. 9 provides a partial cut-away side-elevational view of the spring arrangement of FIG. 8 in a relaxed, contracted condition.

The arrangement illustrated in FIGS. 8 and 9 operates in a similar manner as the arrangement illustrated in FIGS. 3 and 4. A surgical tether (e.g., suture 12) extends between two or more stack members (e.g., spring coils 18c and 18d) of a tether engaging stack structure and is arranged with the stack members to separate at least two of the stack members between which the surgical tether extends when pulled in a first direction (e.g., towards second suture portion 38) but not to separate the at least two stack members when pulled in a second direction (e.g., towards first suture portion 36). In some instances, the stack members may be biased towards one another (e.g., a coil spring) with the stack members permitted to expand in a first direction (e.g., towards a head space defined by a housing) but not in a second direction. As illustrated, in embodiments that use one or more tension coil springs, a portion of the coil spring may simply be secured to the housing, preferably an end of the coil spring, so that expansion of the coil spring is only permitted in a direction extending away from the secured end.

With reference now to FIG. 8 in conjunction with FIG. 9, shown in FIG. 8 is a coil spring 18 in a somewhat extended or expanded configuration (as it might look if the spring 18 was subjected to tension to spread the coils apart) to illustrate another arrangement for the of association of suture 12, and in particular its segment 40, with spring 18. In the illustrated embodiment, the first segment portion 46 of suture segment 40 extends through a lumen defined by coil spring 18. Segment 40 then passes between adjacent spring coils 18a and 18b to thereby extend to a second segment portion 48 that travels external of the spring 18 lumen and along the external surface of multiple spring coils, spring coils 18b and 18c. Similar to the pattern illustrated in FIG. 3, a third segment portion 50 of segment 40 is looped around a spring coil, spring coil 18d, at least one time. Thereafter, unlike in the arrangement illustrated in FIGS. 3 and 4, the fourth segment portion 52 of internalized suture segment 40 extends from the loop(s) segment portion 50 on an opposing side of the spring coils than second segment portion 48 and through the lumen defined by coil spring 18 and ultimately through an opening in the housing.

As will be appreciated, loop segment portion 50 of suture segment 40 may loop around a spring coil in a number of directions. In some instances, for example, suture segment 40 may be wound in a left-handed helix and/or a right-handed helix along a length of one or more spring coils that extend along a helical path towards or away from a first spring end 19 of the coil spring 18. For example, as illustrated in FIGS. 8 and 9, the loop segment portion 50 can extend over the external surface of spring coils 18a, 18b, and 18c before reaching spring coil 18d. After reaching spring coil 18d, the suture segment portion 50 extends along the external surface of spring coil 18d before extending between spring coils 18d and 18e and into the lumen defined by spring 18. When segment portion 50 extends from within the lumen defined by the coil spring 18 (i.e., emerging between spring coils 18c and 18d to form one or more loops), suture segment 40 is positioned to the left side of the second segment portion 48, forming a right-handed helix and extending along a helical path away from the first spring end 19 and segment portion 48.

As illustrated in the FIGS. 8 and 9, the spring coils of the spring 18 are angled (i.e., the helix angle) away from the first spring end 19. As will be appreciated, upon application of a pulling motion on suture portion 38, portions of segment portion 40 extending between spring coils of spring 19 can, in some instances, migrate along a length of one or more spring coils in a helical fashion towards suture portion 38 and/or away from first spring end 19. Should looping segment portion 50 migrate past the top end of the spring 18 and off the end of a spring coil, the suture retention device may no longer operate as intended and may need to be discarded. Advantageously, it has been found that looping segment portion 50 around a spring coil in a direction away from the first spring end 19 and/or an adjacent suture segment closer to the anchor 14, such as a helical path as illustrated in FIGS. 8 and 9, can decrease the migration of the looping segment portion 50 along spring 18 towards the second suture portion 38 and/or away from the first spring end 19 when a pulling force is applied on segment 38 of suture 12, when device 16 is pushed in a direction antegrade along suture 12, or both. As described in more detail above, when such force is applied to the suture 12 and/or the pushing device 16, the coil spring 18 expands and permits travel of the suture 12 relative to the spring 18. By looping the suture segment 40 around a spring coil in a direction away from the segment portion 48, adjacent loop portions or loops of suture segment 40 on a spring coil will tend to spread apart from one another and/or towards the free end of spring 18.

Alternatively, suture segment 40 of FIGS. 8 and 9 may be wound along a length of a spring coil in a direction towards the segment portion 48 (e.g., with the suture segment 40 emerging to the right side of second segment portion 48 from within the lumen). In these instances, the adjacent portions of the suture segment 40 on a coil spring may tend to migrate along a helical length of the spring 18 with the loop portion closer to the first spring end 19 along the helical path of the spring coil pushing the loop portion further from the first spring end 19 towards suture portion 38 upon movement of the coil spring 18 in an antegrade direction along suture 12. However, arrangements prone to migration of looping segment portion 50 are still suitable for the retention of surgical tethers, and the risk of a portion of suture segment 40 disassociating with the spring 18, such as looping segment portion 50 migrating off an end of spring 18, may be decreased by positioning one or more spring coils, such as spring coil 18e, between looping segment portion 50 and suture portion 38, as illustrated in FIGS. 8 and 9, so that looping segment portion 50 must travel a greater helical distance before sliding off an end of the spring 18. Therefore, although it may be preferred in some instances that portions of suture segment 40 that form one or more loops, such as segment portion 50, are helically wound around an axis extending away from segment portion 48 and/or towards segment portion 52, other arrangements are suitable.

Figure 10:
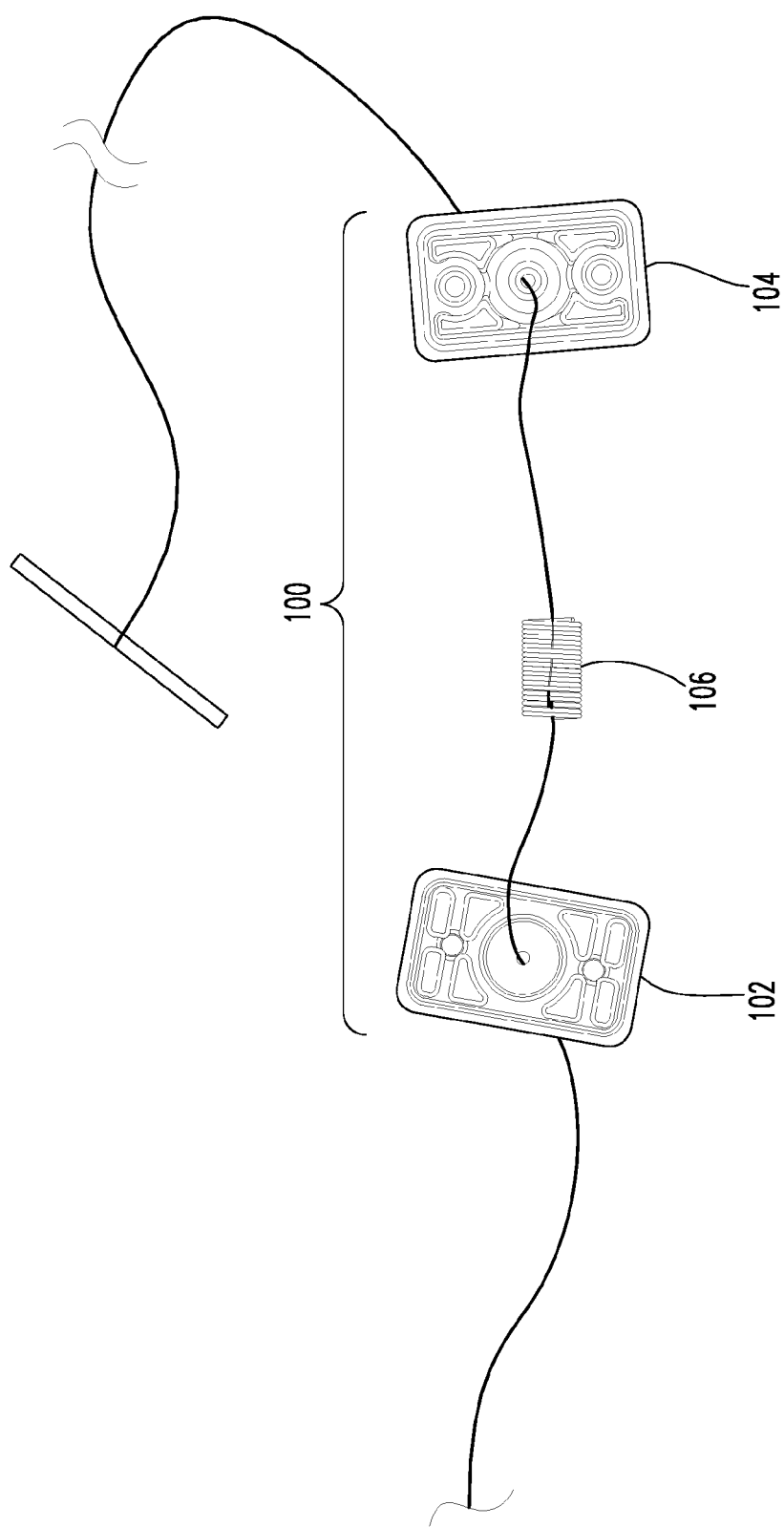
FIG. 10 provides a perspective view of an unassembled suture retention device comprising the spring arrangement of FIGS. 8 and 9.
Figure 11:
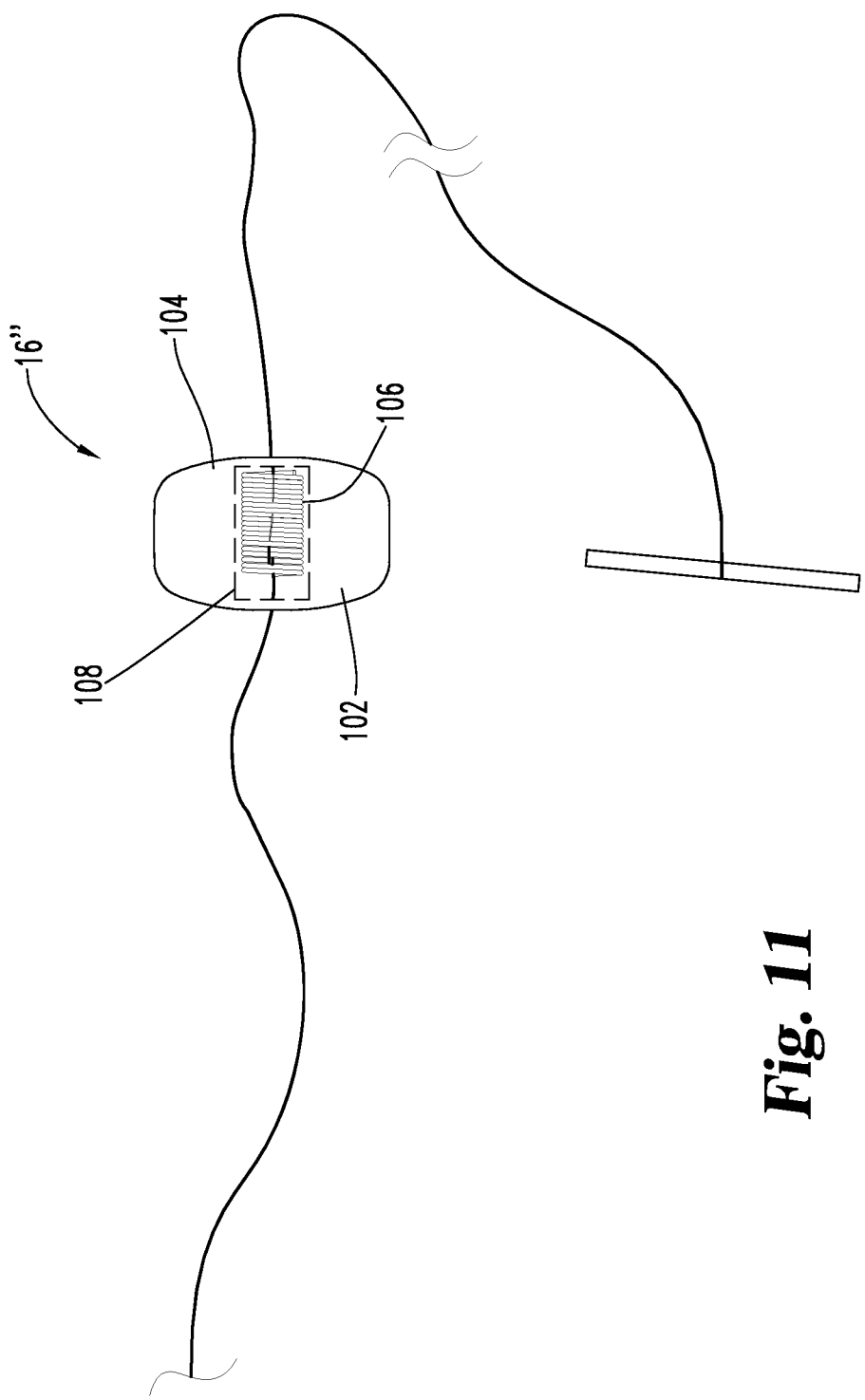
FIG. 11 provides a perspective view of an assembled suture retention device of FIG. 10.

Turning now to another portion of an exemplary surgical tether retention device, FIGS. 10 and 11 illustrate a suture retention deice 100 comprising a first housing member 102, a second housing member 104, and a coil spring 106. First and second housing members 102, 104 are arranged so that the two define an internal chamber 108 arranged to receive the coil spring 106 and allow the expansion thereof. Similar to the device illustrated in FIGS. 1 and 2, first and second housing members 102, 104, when brought into cooperation, can enclose or surround the spring 18 to prevent user or patient contact therewith and can comprise one or more surfaces disposed to face the patient in use. Similarly, spring 18 can be received in internal chamber 108 in a slip-fit or other close-fitting relationship that allows movement along a longitude of the spring 18.

Figure 12A:
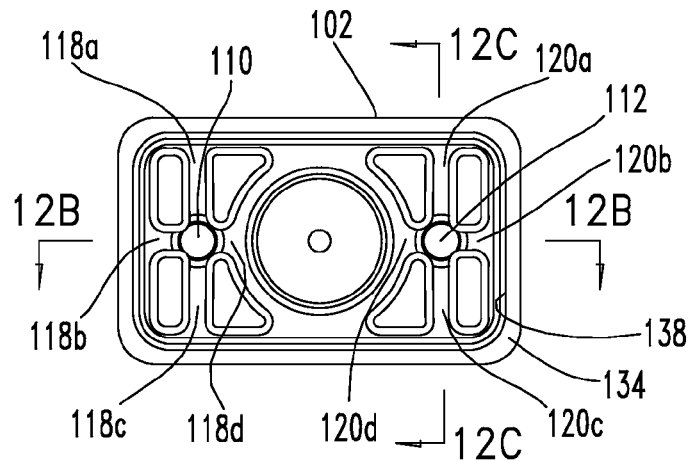
FIG. 12A provides a top plan view of a portion of the device depicted in FIGS. 10 and 11.
Figure 12B:
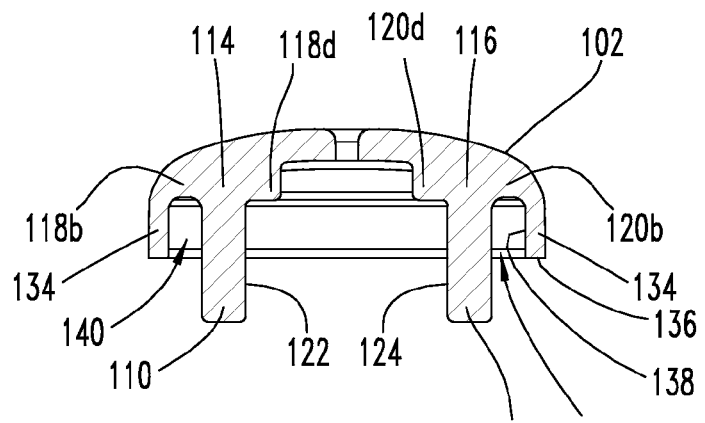
FIGS. 12B and 12C provide partial cross-sectional views of portions of the device depicted in FIG. 12A.
Figure 12C:
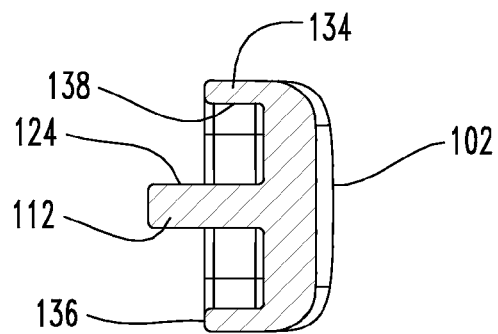

FIGS. 12A, 12B, and 12C illustrate the first housing member 102 in more detail. FIG. 12A illustrates a plan view of the inside of the first housing member 102, and FIGS. 12B and 12C illustrate partial cross-sectional views taken along lines 12B-12B and 12C-12C of FIG. 12A. As illustrated, first housing member 102 comprises a first elongate portion 110 and a second elongate portion 112 that extend in a parallel fashion away from a central portion of the first housing member 102. A first base 114 of the first elongate portion 110 is supported by supporting members 118a, 118b, 118c, and 118d, and, similarly, a second base 116 of the second elongate portion 112 is supported by supporting member 120a, 120b, 120c, and 120d.

A perimeter wall 134 extends around the perimeter of the first housing member 102 and comprises and end surface 136 arranged for contacting a portion of the second housing member 104. Perimeter wall 134 also comprises a side surface 138 that defines recesses 140 and 142 arranged to receive portions of the second housing member 104. Additionally, first and second elongate portions 110, 112 may have side surfaces 122, 124 arranged to contact portions of the second housing member 104.

Figure 13A:
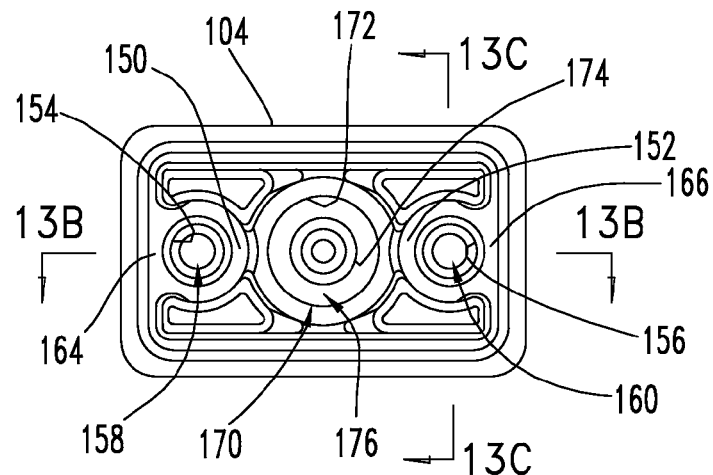
FIG. 13A also provides a top plan view of a portion of the device depicted in FIGS. 10 and 11.
Figure 13B:
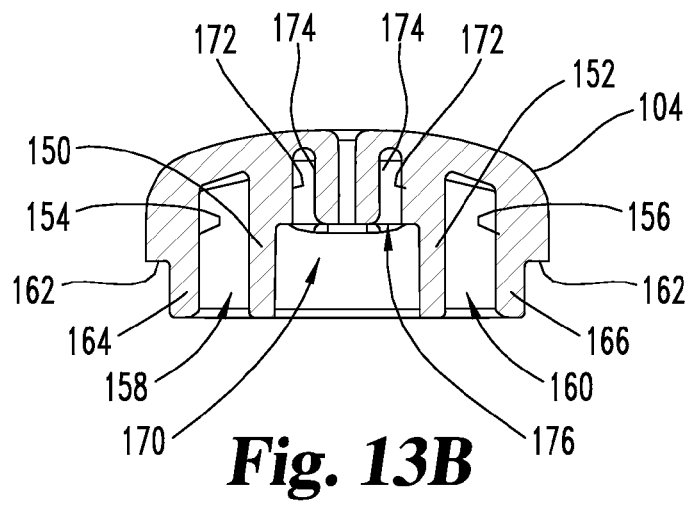
FIGS. 13B and 13C provide partial cross-sectional views of portions of the device depicted in FIG. 13A.
Figure 13C:
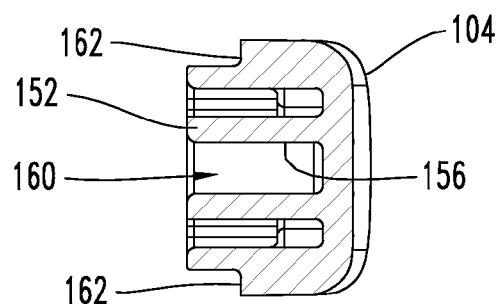

FIGS. 13A, 13B, and 13C illustrate the second housing member 104 in more detail. Similar to FIGS. 12A-C, FIG. 13A illustrates a plan view of the inside of the second housing member 104, and FIGS. 13B and 13C illustrate partial cross-sectional views taken along lines 13B-13B and 13C-13C of FIG. 13A. As illustrated, second housing member 104 has walls 150, 152 with inner surfaces 154, 156 that define recesses 158, 160 arranged to receive the first and second elongate portions 110, 112 of the first housing member 102. In some instances, when the first and second housing members 102, 104 are brought into mating cooperation, inner surfaces 154 and 156 of the second housing member 104 contact side surfaces 122, 124 of the first and second elongate portions 110, 112. Additionally or alternatively, the interaction between surfaces 154, 156 and 122, 124 may be arranged to lock the first and second housing members 102, 104 to one another. For example, one or more of these surfaces of the housing members may be bonded to one another, such as by use of an adhesive, just to name one non-limiting example.

Second housing member 104 also has a perimeter portion defining surface 162 arranged to contact the end surface 136 of perimeter wall 134 of the first housing member 102 and provide a smooth exterior transition between the first and second housing member 102, 104 when the first and second housing members 102, 104 are brought into mating cooperation. Additionally, outer portions 164, 166 of walls 150, 152 can be arranged to coincide with recesses 140, 142 of the first housing member 102 when the housing members 102, 104 are brought into cooperation.

Second housing member 104 comprises a spring retention portion 170. Spring retention portion 170 comprises outside surface 172 and inside surface 174 that define an annular spring receiving recess 176 arranged to receive a first spring end 19 of a coil spring 18 and couple the spring 18 to the second housing member 104. In some embodiments, outside surface 172 of the spring retention portion 170 presses inward on the exterior surface of the spring 18 and/or inside surface 174 extends into the lumen of a spring 18 and presses outward on the interior surface of the spring 18 to couple the spring 18 to the second housing member 104. Additionally or alternatively, as discussed with regards to other embodiments, other mechanical attachments such as set screws and/or adhesives, may be used to fix the relative location of spring 18.

Figure 14A:
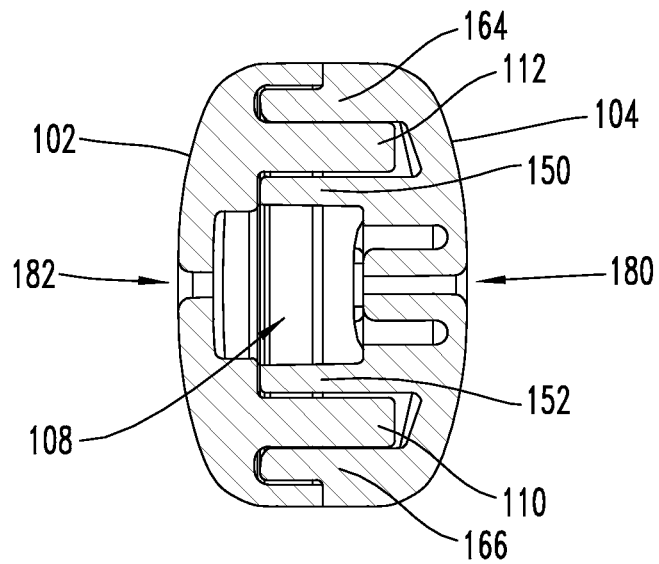
FIGS. 14A and 14B provide partial cross-sectional views of device portions depicted in FIGS. 12B, 12C, 13B, and 13C in contact with one another.
Figure 14B:
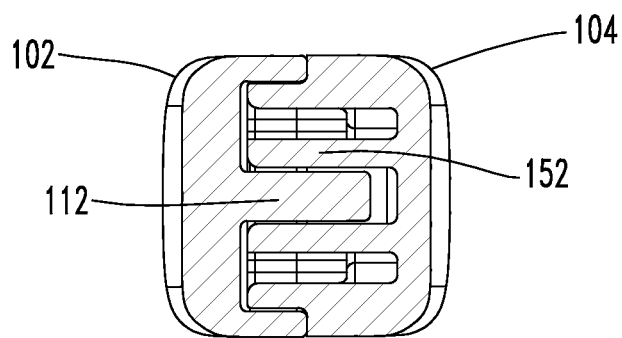

FIGS. 14A and 14B illustrate the first housing member 102 and the second housing member 104 in mating cooperation with one another. As can be seen, the first and second housing members 102, 104 define an internal chamber 108 arranged to receive and allow expansion of a spring 18. Additionally, similar to the other illustrated and disclosed embodiments, openings 180 and 182 allow a surgical tether to extend into the internal chamber 108, such as through opening 180, to associate with a stack members, such as spring coils, and then exit the internal chamber 108 through opening 182.

Descriptions hereinabove have been made with reference to suture 12 as an illustrative and preferred surgical tether. It will be understood, however, that other surgical tether materials are also contemplated in accordance with the invention, including for example any elongate strand or flexible element, the position of which is desired to be secured. These may include, for example, setons, yarns, and elongate natural or synthetic segments, used in surgical procedures. As well, while reference has been made herein to the preferred use of a spring for providing a plurality of closely spaced material segments that cooperate to secure the suture, in other embodiments contemplated, any integral structure or any plurality of separate (non-integral) structures that can move away from or toward one other to cooperate with and releasably engage the suture or other surgical tether as described herein may be used. For example, stack members may be arranged so that when pulled in a first direction (e.g., towards anchor 14) the surgical tether compresses one or more adjacent stack members (e.g., spring coils 18c and 18d) between which a portion of the surgical tether extends and when pulled in a second direction (e.g., towards second suture portion 38) may not compress the one or more adjacent stack members between which it extends and/or separates the one or more adjacent stack members between which it extends, thereby allowing the surgical tether to travel against less frictional resistance.

In further aspects, product embodiments disclosed herein can be enclosed in suitable medical packaging such as trays, pouches, or other enclosing arrangements, and terminally sterilized using any suitable technique. The various products disclosed herein (e.g. suture retention devices, sutures or other tethers with or without attached anchor members, needles, pushers) may be packaged alone or together with one another in such medical packaging. Terminal sterilization techniques may include, as examples, sterilization with ethylene oxide gas (EtO) or by irradiation.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A surgical tether retention device, comprising:
    a housing having a first end and a second end, the first end defining a first end wall surface configured for receipt against an external patient surface and a first end wall opening;
    a tether engaging stack structure retained by the housing, the stack structure including at least first and second adjacent stack members;
    a surgical tether having a housed tether portion extending through the housing in a path from the first end wall opening to a second opening spaced from the first end wall opening;
    the surgical tether having a first external tether portion, the first external tether portion extending out of the first end wall opening in a first direction external of the housing;
    the surgical tether having a second external tether portion, the second external tether portion extending out of the second opening in a second direction different from the first direction and external of the housing;
    wherein the housed tether portion includes at least one tether segment received between the first stack member and the second stack member;
    wherein the housed tether portion is further cooperatively associated with the tether engaging stack so as to urge the first and second stack members away from one another when the housing is urged along the surgical tether in the first direction and to urge the first and second stack members toward one another when the housing is urged along the surgical tether in the second direction; and
    wherein the stack structure comprises a coil spring, and wherein the first and second stack members are first and second coils of the coil spring.

2. The surgical tether retention device of claim 1, wherein the first and second coils of the coil spring apply a clamping force to the tether in the absence of other forced applied to the tether.

3. The surgical tether retention device of claim 2, wherein when the tether is forced in said first direction said clamping force is reduced or eliminated.

4. The surgical tether retention device of claim 1, wherein the surgical tether is a suture.

5. The surgical tether retention device of claim 1, also comprising a surgical tether anchor attached to the first external tether portion.

6. The surgical tether retention device of claim 1, wherein the coil spring has an end positioned within the housing, wherein the housing defines head space adjacent said end of the coil spring, and wherein the coil spring is put under tension and expands when the tether is forced in said first direction so as to move said end of the coil spring into said head space.

7. The surgical tether retention device of claim 1, also comprising a manual release actuator external of the housing, the manual release actuator connected to the tether engaging stack structure and operable upon actuation to urge the first and second stack members away from one another to permit travel of the housing along the surgical tether in the second direction.

8. The surgical tether retention device of claim 1, wherein the housing selectively resists travel along the surgical tether in the second direction relative to the first direction.

9. The surgical tether retention device of claim 1, configured to allow travel of the housing along the surgical tether in the first direction upon the application of no greater than 10 Newtons.

10. The surgical tether retention device of claim 1, configured to prevent travel of the housing along the surgical tether in the second direction upon the application of up to at least 20 Newtons.

11. A device of claim 1, in combination with medical packaging enclosing the device in sterile condition.

12. A surgical method, comprising:
advancing a surgical tether of a device according to claim 1 through patient tissue; and
securing a position of the surgical tether after said advancing.

13. A medical device, comprising:
an elongate surgical tether;
a tether engaging stack structure including at least first and second adjacent stack members, the tether engaging stack structure cooperatively associated with the elongate surgical tether so as to compressively engage and retain the position of the tether relative to the stack when the tether is forced in a first direction relative to the stack but to allow travel of the suture through the stack when the tether is forced in a second direction relative to the stack;
wherein in the absence of force exerted on the stack structure the first and second adjacent stack members apply a clamping force on a segment of the tether; wherein when the tether is forced in said second direction said clamping force is reduced or eliminated; and wherein the tether engaging structure comprises a spring providing the at least first and second adjacent stack members.

14. The medical device of claim 13, also comprising a first wall member having a first wall member opening, and wherein the surgical tether is positioned passing through the first wall member opening.

15. The medical device of claim 13, wherein the tether engaging structure comprises a monolithic structure providing the first and second stack members.

16. The medical device of claim 13, also comprising an anchoring element attached to the surgical tether.

17. The medical device of claim 13, also comprising a needle configured to advance the surgical tether through patient tissue.

18. The medical device of claim 17, wherein the device also includes an anchor attached to the surgical tether, and wherein the needle is configured to advance the anchor through the patient tissue.

19. The medical device of claim 18, wherein the anchor is at least partially received within a lumen of the needle.

20. The medical device of claim 13, also including a housing at least partially enclosing the stack structure.

21. The medical device of claim 20, wherein the housing includes first and second openings at positions spaced from one another, wherein the surgical tether is positioned passing through the housing from the first opening to the second opening, and wherein a segment of the surgical tether within the housing is received between the first and second stack members.

22. The medical device of claim 13, wherein the stack structure includes at least a third stack member, wherein the surgical tether is received between the first and second stack members, and wherein the surgical tether is looped around at least the third stack member.

23. The medical device of claim 22, wherein the portions of the surgical tether extending away from the at least third stack member extend from opposing sides of the at least third stack member.

24. A device for securing a surgical tether, comprising:
(i) a surgical tether;
(ii) an anchoring element attached to the surgical tether; and
(iii) a tether retention device received on the surgical tether, the tether retention device comprising:
a spring having a plurality of spring segments, the plurality of spring segments including at least first and second spring segments adjacent to one another and at least a third spring segment; and
a housing retaining the spring, the housing having a first wall portion defining a first opening and a second wall portion defining a second opening;
wherein the surgical tether passes through the housing of the tether retention device from the first opening to the second opening thereby providing a housed tether segment within the housing, and wherein the housed tether segment is received between the first and second spring segments and looped at least one time around the third spring segment; and
wherein the surgical tether is engaged by the spring such that the suture retention device selectively resists travel along the surgical tether in a second direction relative to a first direction.

25. The device of claim 24, also comprising at least a fourth spring segment, the fourth spring segment located between the second and third spring segments, and wherein the housed tether segment extends over an external surface of the fourth spring segment without looping around the fourth spring segment.

26. The device of claim 25, also comprising at least a fifth spring segment located adjacent the third spring segment, and wherein a portion of the surgical tether passes over an internal surface of the fifth spring segment without looping around the fifth spring segment.

27. The device of claim 25, wherein the spring applies a clamping force onto portions of the housed tether segment in the absence of other applied force to the tether segment.

* * * * *